US008728398B2

(12) United States Patent
Whalen

(10) Patent No.: US 8,728,398 B2
(45) Date of Patent: May 20, 2014

(54) HYDRODYNAMIC ISOLATION METHOD AND APPARATUS

(75) Inventor: Christopher D. Whalen, Pleasant Prairie, WI (US)

(73) Assignee: Sierra Sensors GmbH, Hamburg (DE)

( * ) Notice: Subject to any disclaimer, the term of this patent is extended or adjusted under 35 U.S.C. 154(b) by 396 days.

(21) Appl. No.: 12/964,936

(22) Filed: Dec. 10, 2010

(65) Prior Publication Data

US 2011/0076195 A1 Mar. 31, 2011

Related U.S. Application Data

(62) Division of application No. 11/739,727, filed on Apr. 25, 2007, now Pat. No. 7,858,372.

(51) Int. Cl.
*B01L 3/00* (2006.01)
*G01N 33/00* (2006.01)

(52) U.S. Cl.
USPC ........................... 422/68.1; 422/502; 422/503

(58) Field of Classification Search
USPC ........ 422/401, 425, 502, 503; 506/33, 34, 35, 506/36, 37, 38, 39, 40; 137/803, 806, 814, 137/833
See application file for complete search history.

(56) References Cited

U.S. PATENT DOCUMENTS 5,397,538 A * 3/1995 Stark et al. .................... 422/404

FOREIGN PATENT DOCUMENTS

WO WO 2005024411 A2 * 3/2005

OTHER PUBLICATIONS

Rader, Michael D. et al. "Heterogeneity of the Ro/SSA antigen." Journal of Clinical Investigation 83 (1989) 1293-1298.*
Petersson, Filip et al. "Carrier medium exchange through ultrasonic particle switching in microfluidic channels." Analytical Chemistry 77 (2005) 1216-1221.*

* cited by examiner

*Primary Examiner* — Christopher A Hixson
(74) *Attorney, Agent, or Firm* — Boyle Fredrickson, S.C.

(57) ABSTRACT

The present invention is a flow cell and method for use in microfluidic analyses that presents highly discrete and small volumes of fluid to isolated locations on a two-dimensional surface contained within an open fluidic chamber defined by the flow cell that has physical dimensions such that laminar style flow occurs for fluids flowing through the chamber. This process of location specific fluid addressing within the flow cell is facilitated by combining components of hydrodynamic focusing with site specific cell evacuation. The process does not require the use of physical barriers within the flow cell or mechanical valves to control the paths of fluid movement.

12 Claims, 8 Drawing Sheets

FIG. 4a
PRIOR ART
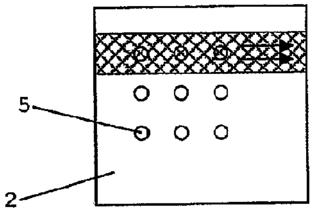
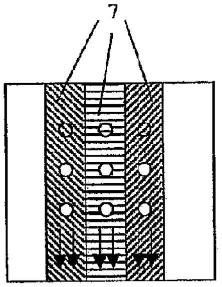
FIG. 4d
PRIOR ART
FIG. 4b
PRIOR ART
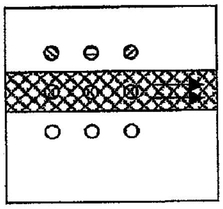
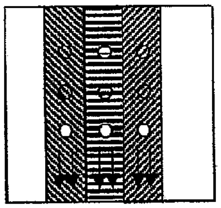
FIG. 4e
PRIOR ART
FIG. 4c
PRIOR ART
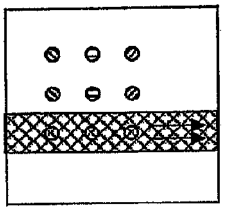
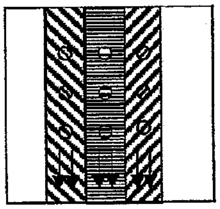
FIG. 4f
PRIOR ART
FIG. 4g
PRIOR ART
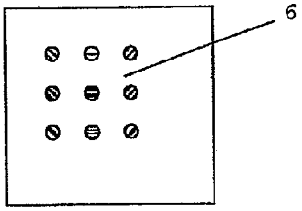

FIG. 11
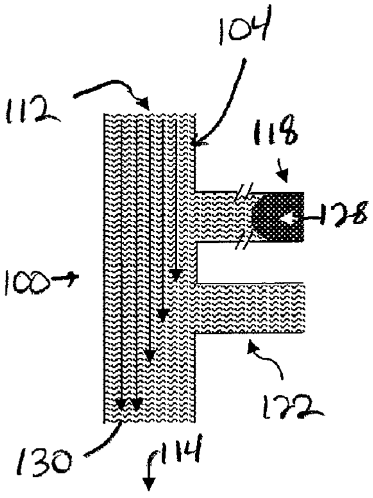
FIG. 12
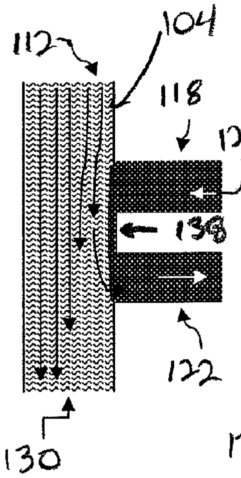
FIG. 13
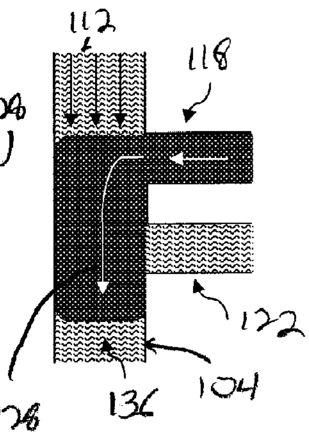
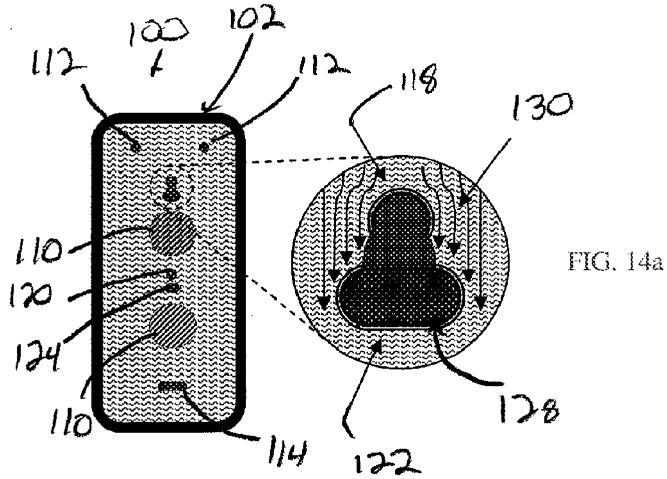
FIG. 14a
FIG. 14

FIG. 16a FIG. 16b FIG. 16c
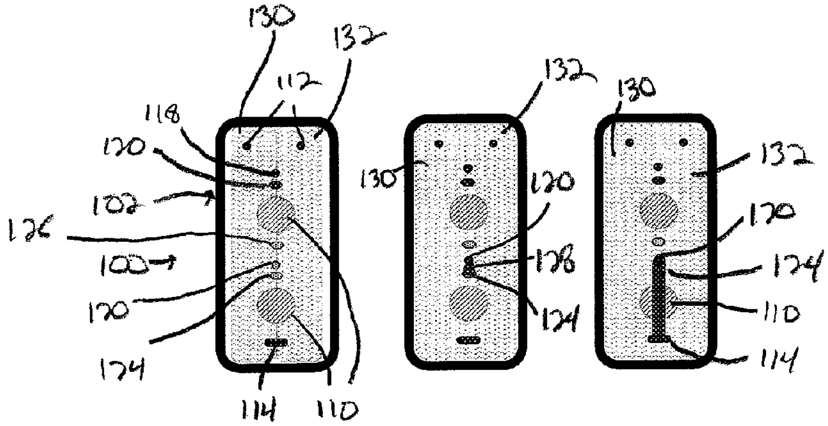
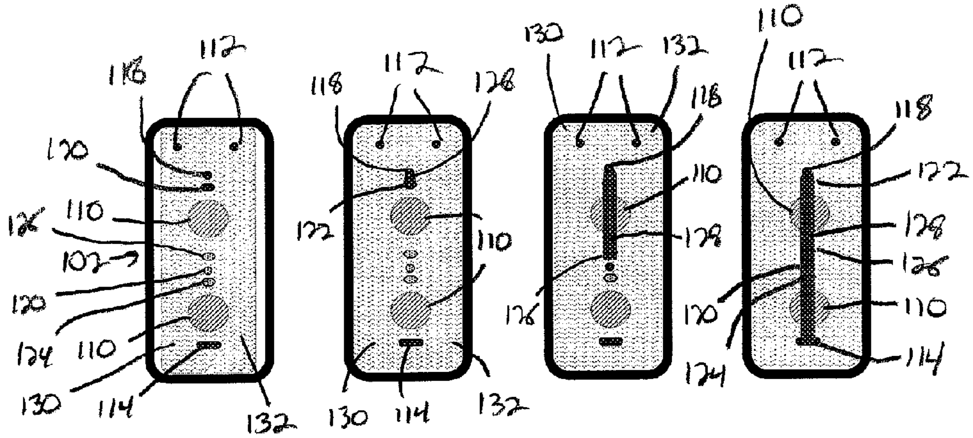
FIG. 15a FIG. 15b FIG. 15c FIG. 15d

HYDRODYNAMIC ISOLATION METHOD AND APPARATUS

CROSS-REFERENCE TO RELATED APPLICATIONS

This application is a division of U.S. application Ser. No. 11/739,727, filed on Apr. 25, 2007 now U.S. Pat. No. 7,858,372, the entirety of which is hereby expressly incorporated by reference herein.

FIELD OF THE INVENTION

The present invention relates to microfluidic devices, and more particularly to such devices that are used in the analytical analysis of fluid samples that include a detection device.

BACKGROUND OF THE INVENTION

In the process of analytical analysis of fluid samples (biologic samples, chemicals reagents, and gases) it is common for test samples to be passed through a chamber containing either a detection substrate, or a transparent window allowing the interrogation of the sample by some form of energy or light. It is common for sample fluids to be delivered and removed from these "detection chambers" using a continuous flow of transport fluid entering the chamber from one end and exiting the chamber at another. Thus these chambers are termed detection "flow cells", and the analysis techniques that utilize them are termed "flow based" detection methods. During flow based analysis, sample fluids to be tested are delivered as discrete volumes, or 'plugs', within a stream of continuously flowing buffer passing through the flow cell and over the detection substrate. The accuracy, sensitivity, and applicability of flow based analysis techniques are highly dependent upon the process and characteristics of the sample fluid delivery to, and removal from, the detection flow cell.

Researchers in a wide variety of fields such as medicinal science and environmental analysis, to name just a few, need to characterize the interactions of biologic molecules found in human, animal, or plant fluids and tissues. These characterizations commonly involve bringing two or more different types of sample molecules into physical contact with each other for a set period of time and then measure if, for example, they have combined to form a molecular complex, or if either has caused a change to the physical structure or function of any of the other reactants. Understanding the kinetics (speed) and affinity (strength) of these molecular interactions are just two of the parameters often measured during these characterization procedures, termed 'molecular interaction analyses'. Typically when utilizing flow cell based analysis techniques during molecular interaction analysis, a population of one of the interacting molecules is permanently attached, or 'immobilized', onto the detection substrate or window within flow cell. Sample containing the other molecule(s) to be investigated are then passed through the flow cell so they have the opportunity to interact with the immobilized molecules and those interactions measured.

So called biosensors, or "label-free" analysis techniques, commonly utilize detection flow cells and flow based sample delivery methods to "present" test samples to be analyzed to the detection sensor surface or substrate. The use of flow based sample delivery in label-free bio sensor instruments can greatly increase the amount of information these techniques can generate about the molecular interactions being investigated. Biacore instruments sold by GE Healthcare are a well known example of label-free analytical biosensors used in biological research for molecular interaction analysis studies. In the case of Biacore instruments, an optical detection technique called Surface Plasmon Resonance (SPR) is employed to measure mass changes on metal surfaces. These mass changes on the sensor surface result from the addition or subtraction of molecules onto the surfaces due to the interaction of molecules with either the sensor surface itself or another molecule attached to the surface. Other examples of analysis techniques that characterize molecular interactions using label-free detection methods include Dipolar Interferometry, Quartz Crystal Microbalance (QCM), Surface Acoustic Wave (SAW), and micro-cantilevers. Aside from eliminating the additional analysis steps, reagents, and sample preparatory requirements of label based testing methods (RIA, ELISA, and Fluorescence techniques), label-free analysis enable the measurement of the molecular interactions under investigation to be recorded as they occur. These real-time analysis capabilities have the potential to provide a great deal of information in addition to confirming the specific binding of target molecules, as is arguably the only capability of label based techniques. Under the proper conditions, real-time, label-free analysis techniques have the ability to determine the speed and strength of molecular interactions, and in some cases, if those interactions resulted in any structural changes to the test molecules. But it has been well documented that these real time analysis capabilities, as well as the accuracy, and sensitivity of label-free detection techniques in general, are highly dependant on the quality of the corresponding flow based sample delivery methods.

For example, one critical aspect of sample delivery in flow cell based analysis techniques is the fast and efficient transition from one reagent to the next within the flow cell. This need for fast and efficient transition between reagents is most clearly demonstrated when characterizing molecules that exhibit very low binding affinity (weak in 'strength') for one another. The association rates (molecules coming together), and dissociation rates (falling apart), termed "kinetic rates", associated with these low affinity interactions often occur within the first few seconds after the test molecules are brought into contact with one another or separated. Thus, the capability to obtain accurate measurements just after the test molecules have come into contact, and immediately following their separation, is crucial to accurate kinetic rate characterization of low affinity molecular interactions.

During automated testing procedures using flow cells, it is commonly advantageous for liquid handling devices to transfer the sample volumes to be analyzed from their storage containers or vials to the chamber or detection flow cell as a plug volume pushed through tubing pathways by another liquid termed the running buffer. As the plug volume of sample liquid is pushed through the tubing of the liquid handling unit, mixing between the plug and the running buffer will often occur creating a volume of liquid at the front and back of the sample plug that is a variable gradient of sample and running buffer. As the concentration of this mixture is unknown, including it in the final analysis of the sample can often interfere with the accuracy and sensitivity of testing.

Thus, it is common for a "cutting" event to be performed on the sample plug volume just prior to its introduction into the analysis chamber. These cutting events typically involve some initial portion of the sample plug volume being directed to a waste just prior to the sample analysis process. Often mechanical valves are used to perform this function but due to limitations in valve technology related to sample waste, valve dimensions, and poor robustness, these structures and methods are not ideal.

Additionally, as the reagent plug enters the flow cell it pushes assay buffer out, with the reverse occurring at the end of the plug injection. During this process, a period of transition occurs where the flow cell, and thus the detection substrate, is exposed to a concentration gradient or mixture of sample and buffer. During these 'transition periods', accurate determination of kinetic rates is not possible as the true concentration of test sample exposed to the detection surface is unknown. Thus, the ability to quickly switch from one fluid to the next within the flow cell during analysis, i.e., the delivery of highly discrete volumes of sample fluid having a clean leading edge without a concentration gradient within a continuous flow of transport fluid, is critical to obtaining as much usable data as possible.

The vast majority of current flow based sample delivery technologies, even on a micro-fluidic level, do an inadequate job of efficiently transitioning between samples or sample and buffer. It is not uncommon for microliters and even ten's of microliters of fluid to pass over the detection surface before contacting solution that is 100% test reagent. As typical test volumes can be less than fifty microliters, flowing at ten's of microliters per minutes, these long transition times severely affect measurement capabilities. The long transition times are mainly due to the physical design of valve technology built into the sample delivery systems, which can often only be effectively utilized at some distance from the flow cell and detection surface. Thus the reagent plug must travel a distance before contacting the detection surface, during which reagent solution mixing will occur. Microfluidic tubing designs employing micro valves have been used with moderate success to overcome this situation as they minimize liquid travel and the micro valves can be located much closer to the detection flow cell. But, due to their design and small size, these valves are costly, often mechanically unreliable, and susceptible to clogging.

Another critical aspect of sample delivery in regards to kinetic rate analysis is the ability for sample molecules to efficiently diffuse from the sample plug onto the sensor surface as the sample plug passes over. It has been well documented that inefficient transport of sample molecules to the sensor surface, termed "mass transport limitations", results in inaccurate estimations of kinetics rates. Efficient molecular diffusion from the sample plug to detection surface is facilitated by passing the sample over the detection substrate as quickly as possible (i.e. fast sample flow rates). But when considering the practical applicability of flow cell based analysis techniques, the requirement to pass sample over the detection surface at high rates of speed becomes a liability.

As the physical nature of molecular interactions often means that sample molecules must be in contact for several minutes to obtain accurate measurements, high sample flow rates during analysis result in the consumption of large volumes of test sample. Historically the most common way to lower sample volume requirements while maintaining high analysis flow rates has been to minimize the size of the detection flow cells. But due to a variety of issues related to the different detection technologies (i.e. size of the detection substrates, electronics, and optics), and the need to interface those technologies with high performance and robust sample fluid delivery systems, there have been practical limitations to the miniaturization of detection flow cells. Thus, with the resource requirements to produce even the crudest biologic samples for testing being very high, and the fact that the new research disciplines such as Proteomics continue to expand the number of samples to be evaluated, there is an ever increasing demand to work with the smallest sample volumes possible.

The next critical aspect when evaluating the applicability of a technology for molecular interaction analysis is the requirement to simultaneously evaluate large numbers of samples while still meeting the requirements of delivering highly discrete, and small volumes of sample at high rates of flow. This process of simultaneous multi-sample analysis is often referred to as High Throughput Sampling, or HTS. Often, based on the analysis methods used in conjunction with HTS, there is a desire in some instances to handle each sample analysis as a completely independent procedure, and in other instances to handle the multiple analyses using exactly the same procedure and reagents. Thus the ultimate applicability for high throughput analysis comes when the user can switch between "individual" and "common" processing of the multiple sample analyses at any time during the testing procedure. Often these variations in testing procedures represent nothing more than different reagents being applied to different test vessels at certain stages of the testing process. For test methods that employ the analysis of molecules coated onto an array surface, this process of individual and common handling of the multiple individual analyses becomes a process of individual and common "addressing" of different reagent fluids to the different locations of the array. In some steps of the assay procedure it is preferable that the same reagent can be addressed to more than one or all of the target locations on the array. In other cases it is desirable to address a different reagent onto each target location.

In the past, a variety of techniques based on the manipulation of the process of Hydrodynamic Focusing have been employed in an attempt to address these requirements. The so called, "Hydrodynamic Addressing" and "Hydrodynamic Guiding" techniques, use guide fluid streams to position sample fluid streams over different sections of array surfaces within flow cell chambers.

One example of a technique of this type is shown in published PCT Publication No. WO/2003/002985, which is incorporated by reference herein and as shown in FIGS. 1 and 2, discloses a method of operating an analytical flow cell device comprising an elongate flow cell having a first end and a second end, at least two ports at the first end and at least one port at the second end, comprises introducing a laminar flow of a first fluid at the first end of the flow cell, and a laminar counter flow of a second fluid at the second end. Each fluid flow is discharged at the first end or the second end, and the position of the interface between the first and second fluids in the longitudinal direction of the flow cell is adjusted by controlling the relative flow rates of the first and second fluids. Also disclosed are a method of analyzing a fluid sample for an analyte, a method of sensitising a sensing surface, and a method of contacting a sensing surface with a test fluid.

Another example is found in PCT Publication No. WO/2000/056444 that is also incorporated by reference herein and as shown in FIG. 3, illustrates a composition of a liquid (26) that is caused to interact with a narrow band shaped area at a chosen position on a solid surface within a flow channel (12) by hydrodynamic focusing of a guided stream of said liquid between two streams of guiding liquid (28). By altering the ratio of the flow rates of the two guiding liquid streams, the position of the guided liquid stream is changed and further interaction with the solid surface takes place along a second band shaped area. Using two such flow channels it is possible to produce a two dimensional array of interaction sites.

Still another example is disclosed in PCT Publication No. WO/2006/050617 which is incorporated by reference herein and illustrates in FIG. 4*a*-4*g* a microfluidic device and its use for the production of micro-arrays, in particular for the detection of protein interactions, is described. The microfluidic device comprises a flow cell part (1) and a chip part (2) together forming at least two crossing, preferably perpendicular, closed channels (3, 4), said flow cell part forming open channels providing the bottom wall and at least part of the side walls, in particular three walls of said closed channels (3, 4), said closed channels (3, 4) being connected to at least three fluid providing means for generating at least three fluid flows (7) and said closed channels (3, 4) being designed and dimensioned such that the flow of at least three aqueous fluids streaming through each of said channels (3, 4) is laminar at least until after said crossing of said channels (6), said chip part (2) forming the top wall and optionally part of said side walls, in particular the fourth wall, of said closed channels (3, 4) and having a surface that is activatable by reaction with an activating molecule.

However, these prior art techniques and structures shown in FIGS. 1-4*g* are limited to addressing sample fluid streams in single dimensions within the array. Thus, if a surface array is viewed as an x-y grid, these techniques can either address only the entire x-row or the entire y-column with a single reagent. These techniques offer no remedy to address individual x-y locations, or "spots", on the array independently severely limiting the flexibility of array design. Thus it is desirable when working with array based testing methods to have the ability to address each test location on the array as a completely individual entity in some instances, and in other instances to treat more than one or all of the test locations in the same manner.

In summary, there remains a considerable need for greater control and flexibility in regards to the volume, speed, and location of reagent presentation to detection surfaces in flow cell based analytical testing technologies.

SUMMARY OF THE INVENTION

According to a first aspect of the present invention, a flow cell device is provided that is capable of operation in a process termed "hydrodynamic isolation" in which highly discrete and small volumes of fluid are presented to isolated locations on a two-dimensional surface contained within an open fluidic chamber that has physical dimensions such that laminar style flow occurs for fluids flowing through the chamber. The device includes a number of reagent inlet ports that are disposed adjacent associated sensor substrates or detection windows. Located between the reagent inlet ports and the detection substrates are reagent evacuation ports. The evacuation ports operate to continuously withdraw a reagent being introduced into a continuous laminar flow of a guide fluid moving along the flow cell through the reagent inlet to enable the reagent to develop a clean leading edge without any appreciable concentration gradient to create problems with regard to the interaction of the sample with the detection substrate (s). Once the clean leading edge of the reagent sample has been created, the vacuum applied to the reagent sample from the evacuation port is stopped, such that the discrete volume reagent sample having the clean leading edge is introduced into the guide fluid flow to move along the flow cell and pass over the detection substrate to interact therewith. Immediately after passing the detection substrate, the reagent sample can be evacuated completely from the flow cell by another evacuation port located downstream from the detection substrate. Thus, the reagent sample is prevented from interacting with any other detection substrate present in the flow cell by removing the reagent sample from the laminar fluid flow moving through the flow cell using a vacuum, without any physical barriers within the cell to divert the fluids, and without the need for mechanical valves, which are difficult to manufacture and break easily. Therefore, the present invention enables discrete volumes of fluids to be injected through a flow cell, or addressed to a specific location within a flow cell, without the need for cumbersome and non-robust valves in the fluid tubing pathways leading up to the fluid inlet ports of the flow cell. This capability enables the design of extremely small array addressing microfluidic devices while maintaining, and in some cases exceeding, the level of functionality of other microfluidic and macrofluidic fluid delivery devices that utilize mechanical valves.

According to another aspect of the present invention, the flow cell device of the present invention is formed to include a number of detection spots or substrates therein in the form of an array, with a reagent inlet port and a reagent evacuation port associated with each detection substrate. In this manner, the flow cell device is able to simultaneously introduce a number of reagent samples within the flow cell, addressing each of the reagent samples to a specific detection substrate, and preventing the intermixing of any of the introduced reagents with one another or with any detection substrates to which they are not addressed. Also, while the reagent inlet and evacuation ports are located and associated with each detection substrate in the flow cell, in one mode of operation it is possible to selectively operate the reagent inlet and evacuation ports to enable reagent samples introduced at separate reagent inlets to travel with the laminar guide fluid flow over multiple detection substrates to obtain multiple interactions of the sample with separate detection substrates prior to evacuating the reagent sample from the flow cell.

According to still another aspect of the present invention, the flow cell is formed with multiple fluid inlets the allow the flow cell to be operated in a manner that allows the guide fluids introduced into the flow cell device through the fluid inlets to be moved across the flow cell through the use of hydrodynamic focusing to enhance the ability of the flow cell to address discrete fluid volumes onto specific spots in the hydrodynamic isolation process. Thus, the reagent samples introduced into the flow cell using the various reagent inlet ports and reagent evacuation ports can additionally be directed to specific detection substrates within the flow cell by the movement of the guide fluid streams into which the reagent samples are introduced prior to being evacuated from the flow cell.

Numerous other aspects, features and advantages of the present invention will be made apparent from the following detailed description taken together with the drawing figures.

BRIEF DESCRIPTION OF THE DRAWINGS

The drawing figures illustrate the best mode of currently contemplated of practicing the present invention.

In the drawing figures:

FIGS. 4*a*-4*g* are schematic views of a third prior art flow cell device;

FIG. 11 is a cross-sectional view of the reagent inlet and evacuation ports of the device of FIG. 5 prior to introducing a reagent sample;

FIG. 12 is a cross-sectional view of the reagent inlet and evacuation ports of FIG. 11 when creating a clean leading edge for the reagent sample;

FIG. 13 is a cross-sectional view of the reagent inlet and evacuation ports of FIG. 11 when introducing the reagent sample into the device;

FIGS. 14 and 14*a* are top plan views of the creation of the clean leading edge for the reagent sample shown in FIG. 12;

FIGS. 15*a*-15*d* are top plan views of a simultaneous hydrodynamic addressing process for each of the detection substrates of the device of FIG. 5;

FIGS. 16*a*-16*c* are top plan views of the hydrodynamic addressing process for a second detection substrate in the device of FIG. 5;

DETAILED DESCRIPTION OF THE INVENTION

Figure 5:
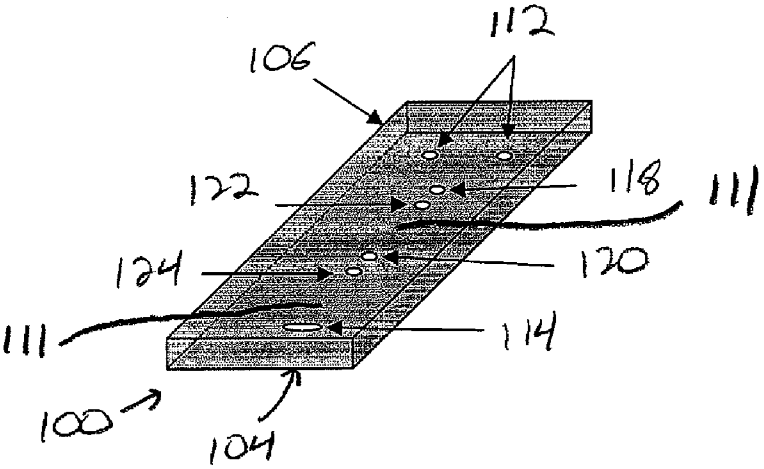
FIG. 5 is an isometric view of a first embodiment of a flow cell device constructed according to the present invention.

Referring now to the drawing figures in which like reference numerals designate like parts throughout the disclosure, a flow cell constructed according to the present invention is illustrates generally at 100 in FIG. 5. While shown as a rectangle in the preferred embodiment, the flow cell 100 can have any shape, as long as the dimensions of the chamber 100 induce laminar flow characteristics in the fluids flowing through the chamber 100, and that the different fluid inlet and outlet or exhaust ports, to be discussed, are located in relation to each other on the chamber 100 such that all the required functions of hydrodynamic focusing and site specific evacuation are possible within the chamber 100.

The flow cell chamber 100 is formed by clamping a liquid sealing gasket 102 of known height between two solid surfaces 104 and 106 that form the large walls of the flow cell 100. Thus, the gasket 102 is formed of a suitably flexible and fluid-impervious material, and forms a single continuous side wall around the periphery of the chamber 100. However, it is also contemplated that substitute engaging or sealing structures (not shown), can be secured to one or both of the surfaces 104 and/or 106, such that the gasket 102 is omitted, or positioned on top of one or more of these structures. These structures can take the form of walls formed integrally with one of the surfaces 104 or 106, or other types of suitable members that are attached in a sealing manner to one of the surfaces 104 or 106.

The large surfaces 104 and 106 are typically formed of any suitable lightweight and fluid-impervious material, and preferably a plastic material, as is known. Further, one of the large surfaces 104 or 106 of the flow cell 100 is made up of a flat surface into which multiple holes or fluid ports 108 have been cut. In FIGS. 5-8, this surface is surface 104. Fluids are delivered into and out of the flow cell through these ports 108, and as such this surface 104 is called the fluid delivery surface 104. There is no requirement all fluid ports 108 must be designed into the same surface 104 or 106 of the flow cell 100. In the above example, the surface 106 that makes up the opposing large wall or ceiling of the flow cell 100 opposite the surface 104 in which the ports 108 are formed is termed the sensor substrate surface, and can be fitted with either sensor substrates or detection windows 110. These sensor substrates or detection windows 110 will constitute the sensor spots 110 within the flow cell 100 and represent the spots to be addressed with reagent using the hydrodynamic isolation process. Additionally, while the illustrated flow cell 100 has the sensor spots 110 on the opposing wall 106 of the flow cell 100, based on the physical dimensions and design of the sensor substrates or detection windows forming the spots 110, the sensor spots 110 could be located on the same wall 104 of the flow cell 100 as that in which the fluid ports 108 are formed. As the disposition of the fluid ports 108 on the surface 104 will define the areas 111 for sample addressing, it is only required that the sensor spots 110 are located in an optimum position within these addressable areas 111.

When the flow cell 100 is formed, the liquid sealing gasket 102 encloses the all fluid ports 108 and sensor spots 110 within the flow cell 100. While the flow cell 100 illustrated contains only two sensor spots 110 on the sensor substrate surface 106, it is contemplated that the flow cell 100 can be formed in a manner to include a sensor substrate surface or surfaces 106 containing hundreds and even thousands of sensor spots 110.

In the first embodiment of the flow cell 100 shown in FIGS. 5-10, the fluid delivery surface 104 is designed such that two main inlet ports 112 are positioned at one end of the fluid delivery surface 104, and a single outlet, or main exhaust port 114 is positioned at the opposing end of the fluid delivery surface 104. During operation of the flow cell 100, continuously flowing guide fluid streams enter the cell through the main inlet ports 112 and, in most instances of operations, will exit the cell 100 through the main exhaust port 114. This design ensures that all fluids entering the cell 100 will flow in a direction from the end of the flow cell 100 where the main inlet ports 112 are located towards the end of the flow cell 100 where the main exhaust port 114 is located. When describing its position within the flow cell 100, the exhaust port 114 is said to be located downstream of the main inlet ports 112. Additionally, the number of inlet ports 112 and outlet ports 114 can be altered as desired, so long as at least one inlet port 112 and at least one outlet port 114 are present to ensure proper movement of the fluids through the flow cell chamber 100.

In this embodiment of the flow cell 100 having only two (2) sensor spots 110, four (4) additional fluid ports 108 are formed within the fluid delivery surface 104. These additional ports 108 are positioned between the main inlet ports 112 and the main exhaust port 114 also formed in the fluid delivery surface 104. In a particularly preferred embodiment, these additional ports 108 are aligned along the central axis 116 of the longest dimension of the flow cell 100, i.e. down the middle of the cell 100. Two of these ports, termed sample or reagent inlet ports (RIPs) 118 and 120, are located downstream of the main inlet ports 112, and just upstream of their respective addressable areas 111 within the flow cell 100. The three other fluid ports 122, 124 and 126 are termed sample or reagent evacuation ports (REPs). REP 122 and REP 124, are each positioned immediately downstream of their corresponding RIP 118 and 120, respectively, such that any fluid entering the flow cell 100 from either RIP 118 or 120 will first pass over the corresponding REP 122 or 124 before contacting any downstream sensor spot(s) 110. REP 126 is located just downstream of the general area of the upstream sensor spot 110 and just upstream of RIP 120. REP 126 allows two independent samples or reagents to be passed over the upstream and downstream sensor spots 110 simultaneously without any mixing of the reagents using the process of hydrodynamic isolation within the flow cell 100, as described below.

Hydrodynamic Isolation Process

A. Control of Sample Fluid Stream Using Hydrodynamic Focusing

A key component of the process of hydrodynamic focusing, as it relates to the present invention, is the ability to control the position and size of a stream of fluid 128 passing through a microfluidic flow cell 100 under conditions of laminar flow, using two or more guide fluid streams 130 and 132.

It is known that when two or more independent streams of fluid flowing under conditions of laminar flow, i.e., the streams each have a low Reynolds number, are in direct contact with each other and flow in the same direction, i.e. parallel to one another, there will be no mixing of the fluid streams other than by diffusion. Also, by varying the rates of flow of the different fluid streams in relation to each other, the size and position of the various streams can be altered. ("Biosensors and Bioelectronics Vol. 13 No. 3-4, pages 47-438, 1998"). In the case where two guide fluid streams 130 and 132 flow on either side of central fluid stream 128, the width of the central fluid stream 128 can be controlled by manipulating the flow rates of the guide fluid streams 130 and 132 in relation to the central fluid stream 128. For example, by changing the rate of flow of the central fluid stream 128 in relation to that of the guide fluid streams 130 and 132, the width of the central fluid stream 128 can be narrowed by decreasing the central stream flow rate, or expanded by increasing the central stream flow rate. Also, by changing the flow rate of one of the guide fluid streams 130 or 132 in relation to the other, the position of the central fluid stream 128 within the flow cell 100 can be shifted from a central location towards either side of the flow cell 100.

Figures 8, 9, 10:
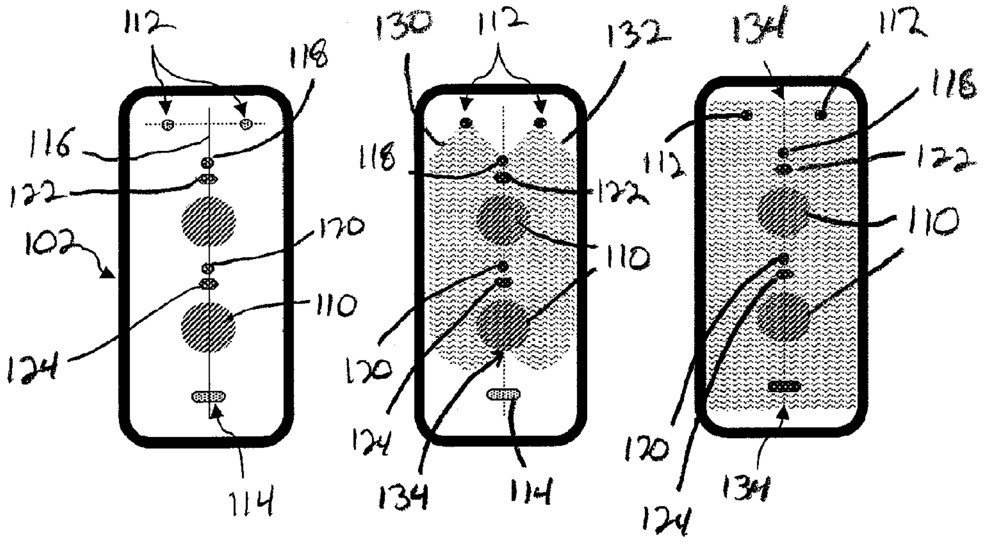
FIG. 8 is a top plan view of the device of FIG. 5 without a guide fluid stream.
FIG. 9 is a top plan view of the device of FIG. 5 with a guide stream being introduced into the device.
FIG. 10 is a top plan view of the device of FIG. 5 with a continuous laminar guide fluid stream flowing therethrough.

As stated previously, the process of hydrodynamic isolation preferably incorporates the use of two guide fluid streams 130 and 132 to control the width and position of a central reagent sample fluid stream 128 introduced into, and flowing within the flow cell 100. FIGS. 8-10 illustrate of the action and flow path of the two guide fluid streams 130 and 132 within the flow cell 100 of the present invention. The guide fluid streams 130 and 132 each enter the flow cell 100 though one of the main inlet ports 112 located at the upstream end of the flow cell chamber 100, and exit the flow cell 100 through the main exhaust port 114 located at the downstream end of the chamber 100. The main inlet ports 112 are optimally positioned along the same x-axis coordinate within the flow cell 100, and are spaced equidistant from the central y-axis of the flow cell 100, along which the others ports 108 present in the cell 100 are preferably aligned. The two guide fluid streams 130 and 132 utilized in the preferred embodiment of the present invention are intended to flow at equal rates of speed at all times during the use of the flow cell 100 in the hydrodynamic process. Due to the laminar nature of the flow of the two guide fluid streams 130 and 132, these streams do not mix because the surface tension for each fluid stream 130 and 132 at the interface 134 of the streams 130 and 132 forms a barrier between the fluid streams 130 and 132 along the interface 134. However, in certain circumstances it is also contemplated that only one guide fluid stream 130 or 132 can be used in the flow cell 100 of the present invention, such as when only one sensor spot 110 is present in the flow cell 100.

During the use of the flow cell 100 in the hydrodynamic isolation process, a reagent sample fluid stream 128 enters the flow cell through one of the RIPs 118 or 120 located on the central axis 116 of the flow cell 100 and downstream of the main flow cell inlet ports 112. The width of the reagent sample fluid stream 128 is determined by its flow rate relative to that of the guide fluid streams 130 and 132. During all stages of sample analysis within the flow cell 100, the flow rate of the sample fluid stream 128 is maintained equal to, or less than, the rate of flow of the guide fluid streams 130 and 132 to ensure proper control of the sample fluid stream 128 by the guide fluid stream 130 and 132.

B. Site Specific Sample Fluid Evacuation

Looking now at FIGS. 11-16*c*, as stated previously, the process of hydrodynamic isolation involves site specific evacuation used in combination with the previously described hydrodynamic focusing to provide the overall function of the hydrodynamic isolation process within the flow cell 100. To facilitate site specific evacuation, the REPs 122-126 described previously are formed in the fluid delivery surface 104 forming a component of the structure of the flow cell 100, and are positioned along the same central axis 116 as that of the RIPs 118 and 120. The REPs 122 and 124 are located downstream of their corresponding RIPs 118 and 120, and upstream of the main fluid outlet port 114 for the flow cell 100. Evacuation of all or a portion of the sample fluid stream 128 within the flow cell 100 is performed by a process of applying suction to the sample fluid stream 128 through the REPs 122 and/or 124 whereby the sample fluid stream 128 is physically removed from the flow cell 128 through the corresponding REP 122 and/or 124 at a rate preferably equal to, or greater than, the rate of flow of the sample fluid stream 128 that is to be evacuated.

The size of the areas 111 which can be addressed by the sample fluid stream 128 downstream of the particular RIP 118 or 120 from which it is introduced into the flow cell 100 is controlled by two factors. These factors are: 1.) the distance between the RIP 118 or 120 and any active downstream REP 122 or 124, or the main exhaust port 114; and 2.) the width of the sample fluid stream 128 as defined by the flow boundaries created by the guide fluid streams 130 and 132. Therefore, the number of locations, or addressable areas 111 within the flow cell which can be independently addressed with different sample fluid streams 128 is dependant upon the number of RIPs 118, 120 and corresponding REPs 122, 124 formed in the fluid delivery surface 104 of the flow cell 100.

Figure 1:
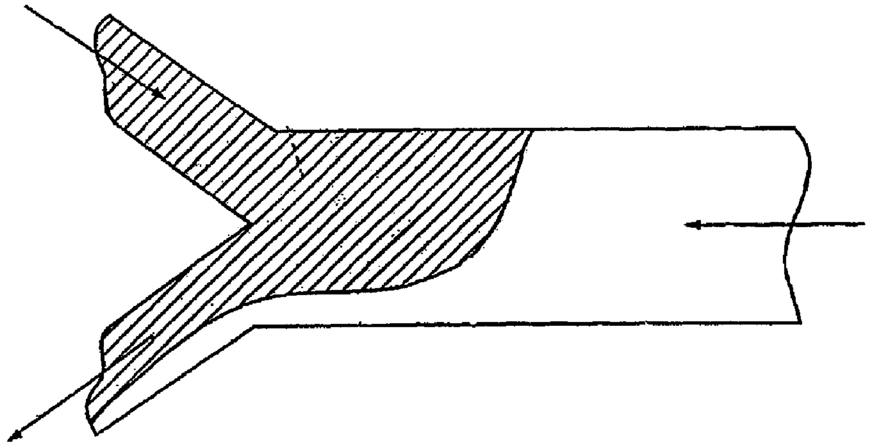
Fig. 1 PRIOR ART
FIG. 1 is a schematic view of a first prior art flow cell device.
Figure 2:
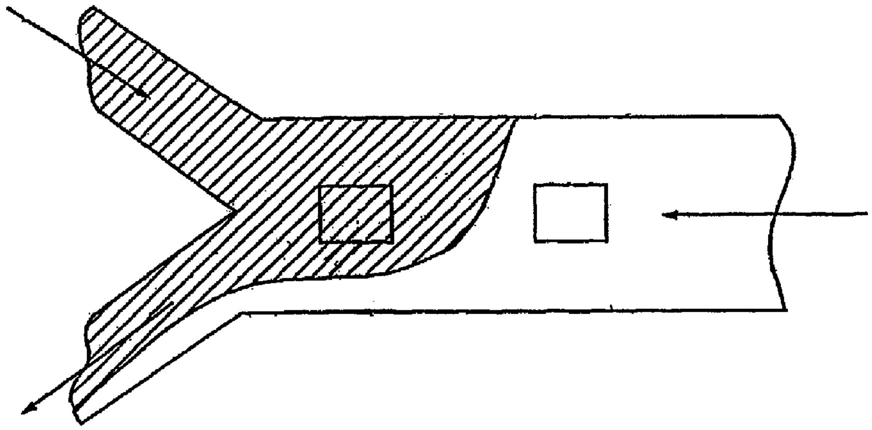
Fig. 2 PRIOR ART
FIG. 2 is a schematic view of the first prior art flow cell device of FIG. 1 including a pair of detection surfaces thereon.
Figure 3:
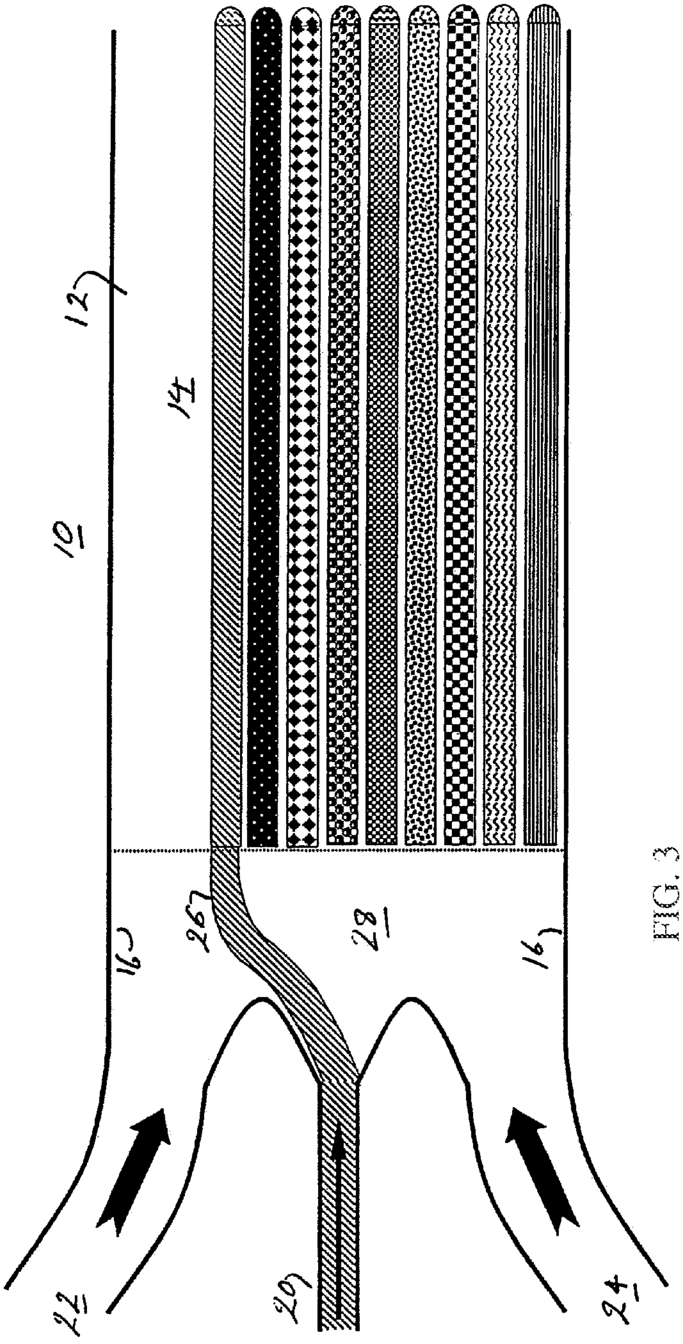
FIG. 3 PRIOR ART
FIG. 3 is a schematic view of a second prior art flow cell design.
Figure 6:
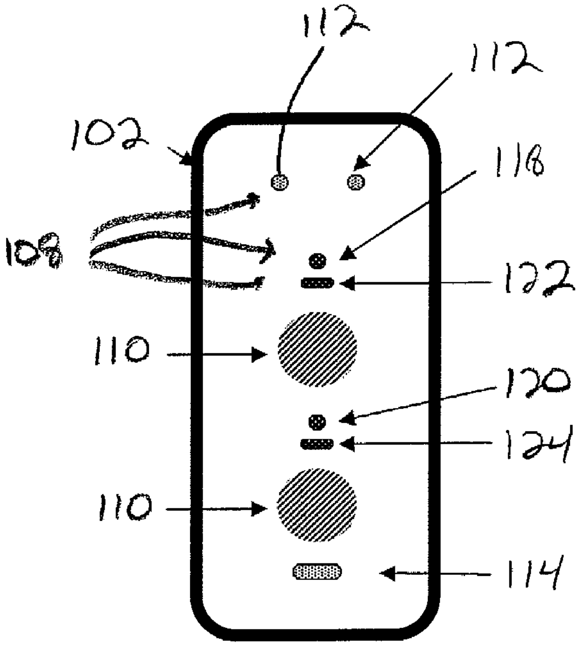
FIG. 6 is a top plan view of the device of FIG. 5.
Figure 7:
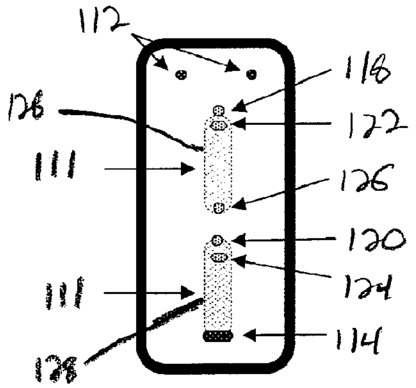
FIG. 7 is a bottom plan view of the device of FIG. 5.

By way of example, in the "2-Spot" flow cell 100 forming the first embodiment of the present invention, best shown in FIGS. 5-7, location specific fluid addressing is possible at two separate locations 111 within the flow cell 100, as well as over an area that is the combination of these two areas 111. To enable this addressing capability, as discussed previously, the fluid delivery surface 104 of the flow cell 100 is formed with two RIPs 118 and 120, and three REPs 122-126. These RIPs 118-120 and REPs 122-126 are aligned along the central axis 116 of the flow cell 100 and downstream of the main inlet ports 112. A pair of REPs 122 and 124 are each located immediately downstream of each RIP 118 and 120 to facilitate the injection of the sample fluid streams 128 associated with each of the RIPs 118 and 120. (See FIGS. 6 and 7) Another REP 126 is formed in the fluid delivery surface 104 between the REP 122 and the RIP 120, such that the REP 126 is associated with the RIP 118 and enables the evacuation of the sample fluid stream 128 that has passed over the upstream detection spot 110 prior to this stream 128 passing over RIP 120, REP 124, and the downstream detection spot 110.

i.) Addressing Upstream Spot Only or Upstream and Downstream Spots

To address either the upstream spot 110, or both the upstream and downstream spots 110, the hydrodynamic isolation process begins with the two streams of guide fluid 130 and 132 being introduced into the flow cell 100 through the fluid inlets 112 to flow at the same rate of speed, passing the guide fluid streams 130 and 132 through the interior of the flow cell 100, and then discharging the guide fluid streams 130 and 132 from the flow cell 100 through the main fluid outlet port 114. While the initial charging of the flow cell 100 with the guide fluid streams 130 an 132 can be done with these fluid streams 130 and 132 in any suitable manner, it is essential that once a sample or reagent fluid stream 128 is ready to be introduced into the flow cell 100, the guide fluid streams 130 and 132 must continuously flow through the flow cell 100 at an equal rate of speed.

To address the upstream spot 110, or the combination of the upstream and downstream spots 110 with a sample fluid stream 128, the sample fluid enters the flow cell 100 through RIP 118.

As best illustrated in FIGS. 11-15*d*, in the hydrodynamic isolation process, a portion of the sample plug volume or fluid stream 128 is directed to waste just prior to analysis. The flow cell 100 is designed such that a REP 122 or 124 is always located between a RIP 118 or 120 and the downstream spot 110 where addressing of the sample fluid stream 128 is to occur. Thus, as the leading edge 136 of the sample fluid stream 128 enters the flow cell 100 through the RIP 118, it is immediately directed over its corresponding REP 122, where the leading edge 136 can be evacuated from the cell 100. (See FIGS. 12 and 15*b*).

Additionally, as the sample fluid stream 128 enters the flow cell 100, its width and flow path are controlled by the guide fluid streams 130 and 132, forcing the sample fluid stream 128 to flow along the central axis 116 of the cell 100. (See FIG. 14*a*) The rate of flow of the sample fluid stream 128 relative to that of the guide fluid streams 130 and 132 is set to a velocity such that the width of the sample fluid stream 128 is at least equal to, and preferably narrower than, the orifice of the downstream REPs 122 or 124. FIGS. 14 and 14*a* illustrate how the combination of the hydrodynamic focusing provided by the guide fluid streams 130 and 132, and the site specific evacuation provided by the REP 122 ensures the initial sample-buffer mixture present at the leading edge 136 of the sample fluid stream 128 will not come in contact with any other areas of the flow cell 100. While the preferred embodiment calls for the REP 122-126 to be at least as large as the corresponding RIP 118, 120, it is possible for the REP 122-126 to be made smaller than the RIP 118 or 120, so long as the rate of evacuation through the REP 122-126 is sufficient to withdraw all of the sample fluid flow 128 through the REP 122-126. Also, for those flow cells 100 designed to address only one spot 110, only a single RIP 118 is required with a single corresponding REP 122 for evacuation of the leading edge 136 of the stream 128. This is because the remainder of the stream 128 can simply be evacuated from the flow cell 100 along with the guide fluid streams 130 and 132 at the main fluid outlet 114.

FIGS. 11-13 illustrate in more detail how this process of valveless switching employing the REPs 122-126 is used to redirect sample fluid streams 128 without the need for in-tubing valves or mechanical barriers in the flow cell 100. Away from the flow cell 100, a volume of the sample fluid, or a sample plug is transferred into some form of sample handling unit which will push the sample fluid through a tubing pathway (not shown), using a flow of running buffer, until it reaches a sample loop 138 just prior to the flow cell 100. As the sample fluid volume 128 fills the sample loop 138 and approaches the RIP 118 in the flow cell 100, evacuation through the REP 122 located just downstream of the RIP 118 is initiated. The sample fluid stream 128 enters the flow cell 100 at a flow rate that is extremely slow relative to that of the guide fluid streams 130 and 132. This slow rate of flow confines the size of the sample fluid stream 128 formed in the flow cell 100 such that it is at least equal to or smaller than the diameter of the corresponding REP 122, as described previously. (See FIG. 14*a*). Also the rate of evacuation of the sample fluid stream 128 through the REP 122 is such that the entire sample fluid stream 128 is removed from the cell through the REP 122. After the sample-buffer mixture at the leading edge 136 of the sample fluid stream 128 has been evacuated to waste, evacuation through the REP 122 is stopped, and the sample fluid stream 128 is allowed to flow to other areas of the flow cell 100. (See FIGS. 13 and 15*c*). Once past the REP 122, the path and size of the sample fluid stream 128 is then controlled by its rate of flow relative to that of the guide fluid streams 130 and 132. Once the sample fluid stream 128 has interacted with and passed the upstream spot 110, the REP 126 is activated as the sample fluid stream 128 approaches to evacuate all of the stream 128 in a manner similar to that done for the leading edge 136 upon injection of the stream 128, to prevent the stream 128 from coming into contact with the downstream spot 110. (See FIG. 15*c*).

Additionally, in some situations when sample plugs are pushed through the tubing pathways of the sample handling unit, one or more air bubbles (not shown) will be used to separate the sample plug from the running buffer. These air bubble separators can greatly reduce sample-buffer mixing during transfer, but often they can cause major interference in the detector response signal if allowed to come in contact with the detection substrate or spot 110. The process of valveless switching using the hydrodynamic isolation process in the flow cell 100 as previously described can be used to redirect these air bubble separators to waste prior to sample analysis within the flow cell 100.

To address the sample fluid stream 128 over the combination of both the upstream and downstream spots 110, termed a "non-evacuation" event, as best shown in FIG. 15*d*, the sample fluid stream 128 enters through RIP 118 and is allowed to flow to the main exhaust port 114 of the flow cell 100. The sample fluid stream 128 is not acted upon by any of the REPs 122-126, except during the evacuation of the leading edge 136 of the stream 128 as described previously, such that the stream 128 exits the flow cell 100 at the main fluid outlet port 114, along with the guide fluid streams 130 and 132 due to the pressure differential created by the force of the fluid streams 128-132 filling the enclosed flow cell 100. In this case the "spot" in the flow cell 100 that is addressed by the sample fluid stream 128 extends from RIP 118 all the way to the outlet port 114, as best shown in FIG. 15*d*. Additionally, in a flow cell 100 adapted for this method of operation, the RIP 120, and REPs 124 and 126 can be omitted from the flow cell 100.

ii.) Addressing Downstream Spot Only

As illustrated in FIG. 16*a*-16*c*, to address the sample fluid stream 128 across only the downstream spot 110, the sample fluid stream 128 enters the flow cell 100 through RIP 120 in the manner described previously regarding the introduction of the sample fluid stream 128 through the RIP 118. (See FIG. 16*b*) As the sample fluid stream 128 enters the flow cell 100, its width and flow path are controlled by the guide fluid streams 130 and 132 forcing the sample fluid stream 128 to flow along the central axis 116 of the flow cell 100 and over the downstream spot 110. After passing the downstream spot 110, the sample fluid stream 128 then exits the flow cell 100 through the main fluid outlet port 114 along with the guide fluid streams 130 and 132. (See FIG. 16*c*).

Hydrodynamic Isolation in Multi-Spot Arrays

Figure 17:
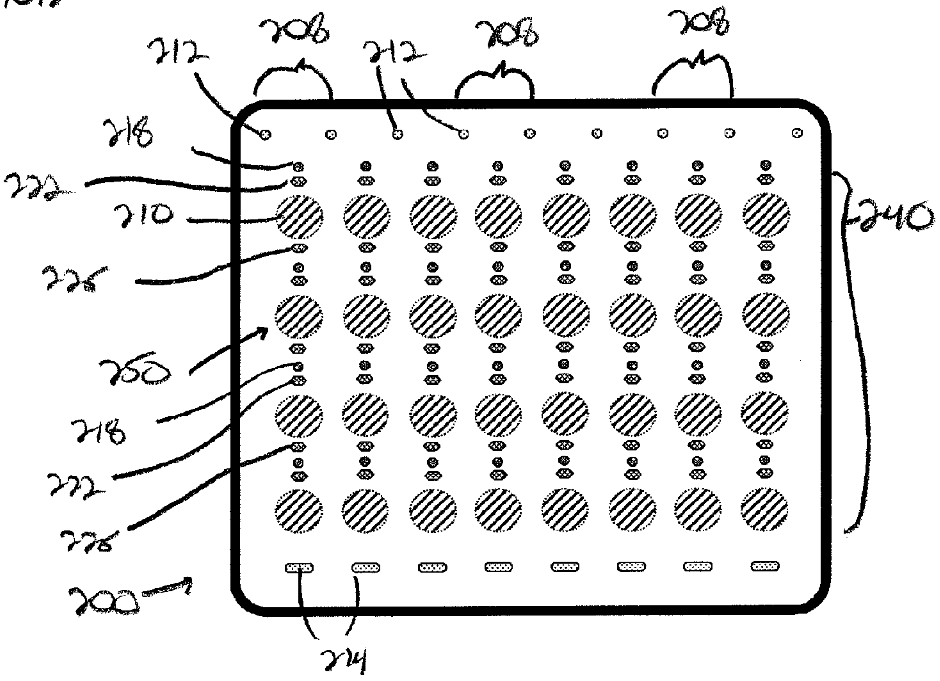
FIG. 17 is a top plan view of a second embodiment of the device of FIG. 5.

While the first embodiment of the present invention illustrates the use of the flow cell 100 in a hydrodynamic isolation process to address sample fluid streams 128 over two separate sensor spots 110, and the combination of those sensor spots 110, in a second embodiment of the present invention illustrated in FIG. 17, the flow cell 200 is constructed with having multiple addressable sensor spots 210 forming a spot array 250. The flow cell 200 has a greater length than the flow cell 100, and correspondingly a longer central axis 216 than the previous embodiment for the flow cell 100, such that the cell 200 can be formed with the array 250 including multiple addressable sensor spots 210 and corresponding sets of fluid ports 208, i.e., RIPs 218 and REPs 222 and 226, along the longer central axis 216. The number of separately addressable spots 210 in the array 250 within the flow cell 200 is determined by the total number of RIPs 218 and corresponding REPs 222 and/or 226 provided in the fluid delivery surface 204 of the flow cell 200.

In addition, the width of the flow cell 200 can be extended, such that multiple copies of the array 250 can be repeated in a grid-like pattern 240, with each added set of fluid ports 208 further including additional fluid inlets 212 and fluid outlets 214 to create a large array of individually addressable 210 within a single open flow cell 200. FIG. 17 illustrates a top down view of a thirty-two (32)-spot array configuration for the flow cell 200. However, it is also contemplated that flow cells 200 having an array 250 including any number of spots 210 could be formed as well.

Two-Dimensional Hydrodynamic Isolation

Figure 18:
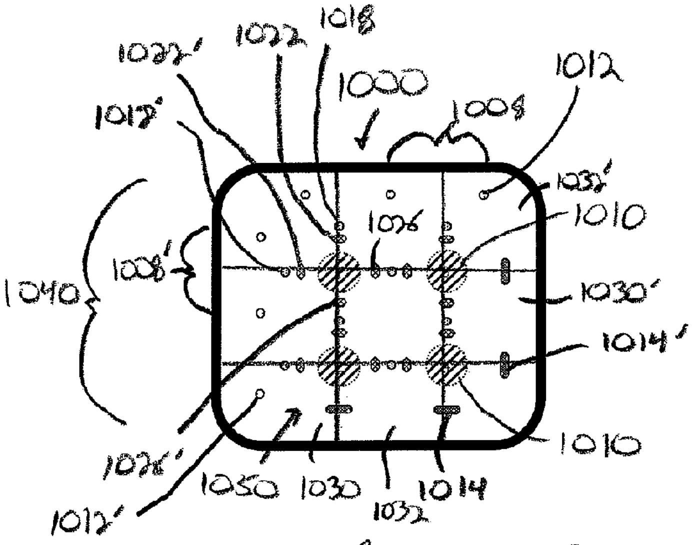
FIG. 18 is a top plan view of a third embodiment of the device of FIG. 5.

Looking now at FIG. 18, a third embodiment of the flow cell 1000 of the present invention is illustrated in which the flow cell 1000 is capable of location specific addressing of sample fluid streams over a two (2) dimensional sensor spot array 1050 formed in the flow cell 1000. The flow cell 1000 includes sensor spots 1010 oriented in a grid-like pattern 1040 to form an array 1050, similarly to the flow cell 200, with a corresponding set of fluid ports 1008, i.e., fluid inlets 1012, fluid outlet 1014, RIPs 1018 and REPs 1022, 1026, oriented along each column of the spot array 1050. However, the flow cell 1000 also includes an additional set of fluid ports 1008' disposed along each row of the spot array 1050 and oriented generally perpendicular to the set of fluid ports 1008 disposed along the columns of the array 1050. The various apertures forming the row sets 1008', i.e., the fluid inlets 1012', fluid outlet 1014', RIPs 1018', and REPs 1022', 1026', function identically to the corresponding members in the column sets 1008, such that sample fluid streams can be addressed to individual spots 1010 of the array 1050 in either the rows of spots 1010 or columns of spots 1010 formed in the array 1050.

As stated previously, one advantage of the design of the flow cell of the present invention is the ability to address fluids over multiple locations individually or concurrently in an open cell format by using the configuration of the ports formed in the flow cell in conjunction with hydrodynamic focusing employing the guide fluid streams. The ability to address individual spots is further enhanced in the flow cell 1000 as a result of the multiple guide fluid streams 1030, 1032, 1030' and 1032' that are positioned within the flow cell 1000 at ninety (90) degrees with respect to one another. By varying the flow rates for each guide fluid stream 1030, 1032, 1030' and 1032' in the flow cell 1000, it is possible to move sample fluid streams not only along the rows and columns of spots 1010 of the array 1050, but in virtually any direction, e.g., diagonally, across the array 1050 to address selected spots 1010 on the array 1050. In conjunction with this ability, it is also contemplated that additional sets of ports can be formed in the flow cell 1000, such as a set of ports oriented forty-five (45) degrees with respect to each of the rows and columns of the array 1050, to enable more direct introduction and movement of sample fluid streams along directions other than along the rows and columns of the array 1050. In short, the flow cell 1000 expands the ability to address sample fluid streams to specific sensor spots 1010 by enabling concurrent fluid addressing events over a wider variety of combinations of addressable spots 1010 within the array 1050.

Various alternatives to the present invention are contemplated as being within the scope of the following claims particularly pointing out and distinctly claiming the subject matter regarded as the invention.

I claim:

1. A fluid flow cell for use in analysis of fluid samples, the flow cell comprising:

a) a housing having a number of fluid-guiding surfaces forming the housing and a fluid flow path through the housing;
b) at least one fluid inlet disposed in one of the fluid-guiding surfaces along the fluid flow path;
c) at least one fluid outlet disposed in one of the fluid-guiding surfaces along the fluid flow path and spaced from the at least one fluid inlet;
d) a first reagent inlet port disposed in one of the fluid-guiding surfaces along the fluid flow path;
e) a first reagent evacuation port disposed in one of the fluid-guiding surfaces along the fluid flow path immediately downstream from the first reagent inlet port; and
f) a detection substrate disposed within the housing along the fluid flow path and spaced from the first reagent inlet port and the first reagent evacuation port, wherein the detection substrate is located within the housing along the fluid flow path between the first reagent evacuation port and the at least one fluid outlet.

2. The flow cell of claim 1 wherein the detection substrate is disposed on a fluid-guiding surface opposite the fluid-guiding surface in which the first reagent inlet port and the first reagent evacuation port are disposed.

3. A fluid flow cell for use in analysis of fluid samples, the flow cell comprising:

a) a housing having a number of fluid-guiding surfaces forming the housing and a fluid flow path through the housing;
b) at least one fluid inlet disposed in one of the fluid-guiding surfaces along the fluid flow path;
c) at least one fluid outlet disposed in one of the fluid-guiding surfaces along the fluid flow path and spaced from the at least one fluid inlet;
d) a first reagent inlet port disposed in one of the fluid-guiding surfaces along the fluid flow path;
e) a first reagent evacuation port disposed in one of the fluid-guiding surfaces along the fluid flow path adjacent the first reagent inlet port; and
f) a detection substrate disposed within the housing along the fluid flow path adjacent the first reagent evacuation port opposite the first reagent inlet port.

4. The flow cell of claim 3 wherein the first reagent evacuation port is disposed between the at least one fluid inlet and the at least one fluid outlet.

5. The flow cell of claim 3 wherein the first reagent inlet port is disposed between the at least one fluid inlet and the at least one fluid outlet.

6. The flow cell of claim 3 wherein the first reagent evacuation port is dimensioned to be at least as wide as the first reagent inlet port.

7. The flow cell of claim 3 further comprising:

a) a second reagent inlet port disposed in one of the fluid-guiding surfaces and space from the first reagent inlet port; and b) a second reagent evacuation port disposed in one of the fluid-guiding surfaces and spaced from the first reagent evacuation port.

8. The flow cell of claim 7 wherein the first reagent inlet port, the second reagent inlet port, the first reagent evacuation port and the second reagent evacuation port are disposed along a single row or column of the housing.

9. The flow cell of claim 7 wherein the first reagent inlet port and the first reagent evacuation port are disposed perpendicularly to the second reagent inlet port and the second reagent evacuation port.

10. The flow cell of claim 7 further comprising a third reagent evacuation port disposed between the first reagent evacuation port and the second reagent inlet port.

11. The flow cell of claim 1 further comprising:

a) a plurality of reagent inlet ports disposed in one of the fluid-guiding surfaces; and b) a plurality of reagent evacuation ports disposed in one of the fluid-guiding surfaces; and c) a plurality of detection substrates disposed within the housing and spaced from each of the plurality of reagent inlet ports and the plurality of reagent evacuation ports.

12. The flow cell of claim 1, wherein the first reagent evacuation port is disposed between the at least one first reagent inlet port and the detection substrate upstream from the at least one fluid outlet.

* * * * *